United States Patent
Jessop

[11] Patent Number: 5,901,748
[45] Date of Patent: May 11, 1999

[54] SELECTOR VALVE

[75] Inventor: Adrian Jessop, Northwich, United Kingdom

[73] Assignee: Proteus Developments Limited, Northwich, United Kingdom

[21] Appl. No.: 08/545,711

[22] PCT Filed: May 18, 1994

[86] PCT No.: PCT/GB94/01064

§ 371 Date: Dec. 19, 1995

§ 102(e) Date: Dec. 19, 1995

[87] PCT Pub. No.: WO94/27070

PCT Pub. Date: Nov. 24, 1994

[30] Foreign Application Priority Data

May 19, 1993 [GB] United Kingdom .................... 9310301

[51] Int. Cl.⁶ ................................................. F16K 11/074
[52] U.S. Cl. .................................. 137/625.11; 73/863.81
[58] Field of Search .................... 137/625.11; 73/863.81, 73/863.85, 863.86

[56] References Cited

U.S. PATENT DOCUMENTS

| | | | |
|---|---|---|---|
| 759,688 | 5/1904 | Frazier | 137/627.47 X |
| 2,516,425 | 7/1950 | Sarver | 137/625.11 |
| 2,821,998 | 2/1958 | Mayhew | 137/625.11 |
| 3,508,582 | 4/1970 | Aulisa | 137/625.11 |
| 3,556,153 | 1/1971 | Barbuto | 137/625.47 |
| 3,995,494 | 12/1976 | Muller et al. | 137/625.11 X |
| 4,191,213 | 3/1980 | Dölling et al. | 137/625.11 X |
| 4,198,964 | 4/1980 | Honneffer | 128/87 R |
| 4,429,717 | 2/1984 | Montgomery | 137/625.47 |
| 4,545,408 | 10/1985 | Sonneborn | 137/625.46 |
| 4,785,676 | 11/1988 | DeOca et al. | 76/863.85 |
| 4,928,539 | 5/1990 | Champseix et al. | 73/863.852 X |
| 4,989,641 | 2/1991 | Jones et al. | 137/625.11 |
| 4,998,954 | 3/1991 | Burr | 73/863.86 X |
| 5,046,522 | 9/1991 | Devehat et al. | 137/625.11 X |

FOREIGN PATENT DOCUMENTS

| | | |
|---|---|---|
| 285 408 | 10/1988 | European Pat. Off. . |
| 837443 | 6/1960 | United Kingdom . |
| 895518 | 5/1962 | United Kingdom . |
| 995016 | 7/1965 | United Kingdom . |
| 87/02428 | 4/1987 | WIPO . |

Primary Examiner—John Rivell
Attorney, Agent, or Firm—Oliff & Berridge, PLC

[57] ABSTRACT

A selector valve includes an annular body having a sealing surface having a plurality of inlet ports. The sealing head carries a seal member which is urged by a spring against the sealing surface. The sealing member has a sealing face comprising a central band and lateral areas above and below the central band. The lateral areas are reduced in size compared to the area of the central band to equalize wear of the sealing member.

19 Claims, 5 Drawing Sheets

U.S. Patent    May 11, 1999    Sheet 1 of 5    5,901,748
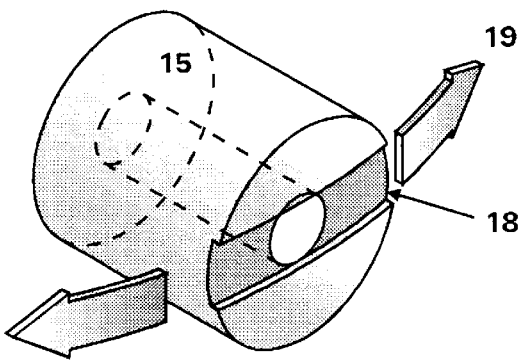
Fig. 3 Prior Art
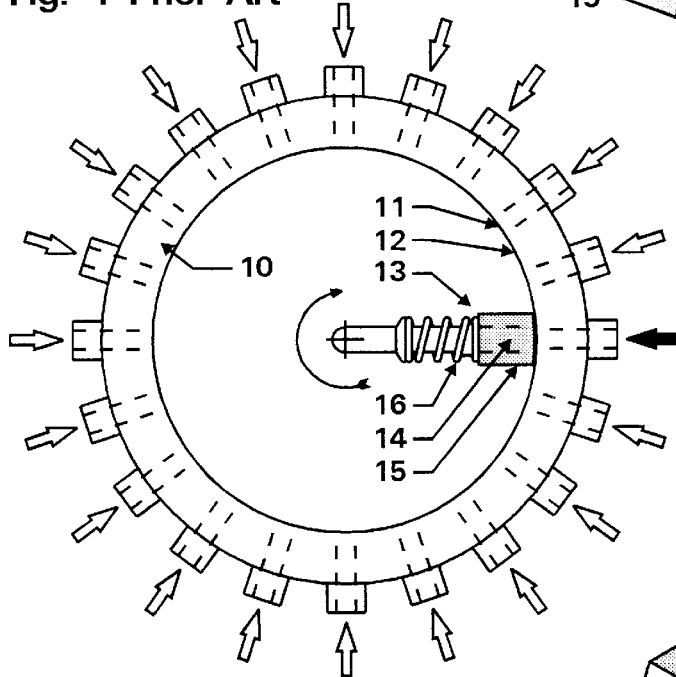
Fig. 1 Prior Art
Fig. 2 Prior Art
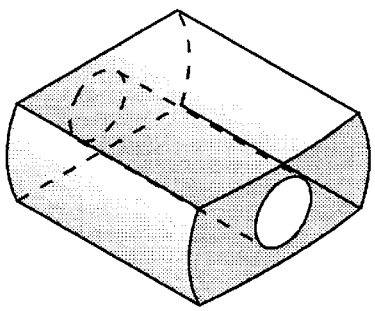
Fig. 5b
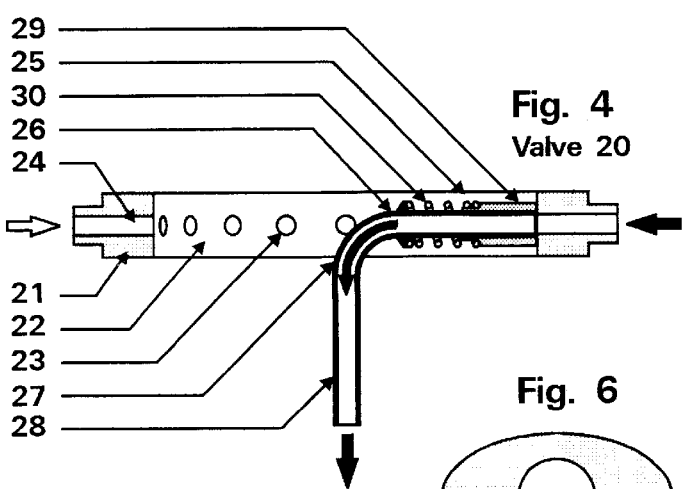
Fig. 4
Valve 20
Fig. 5
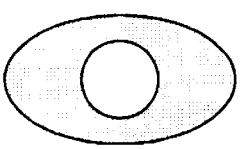
Fig. 6
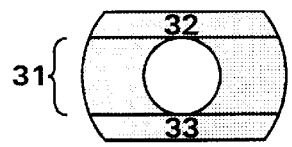
Fig. 5a

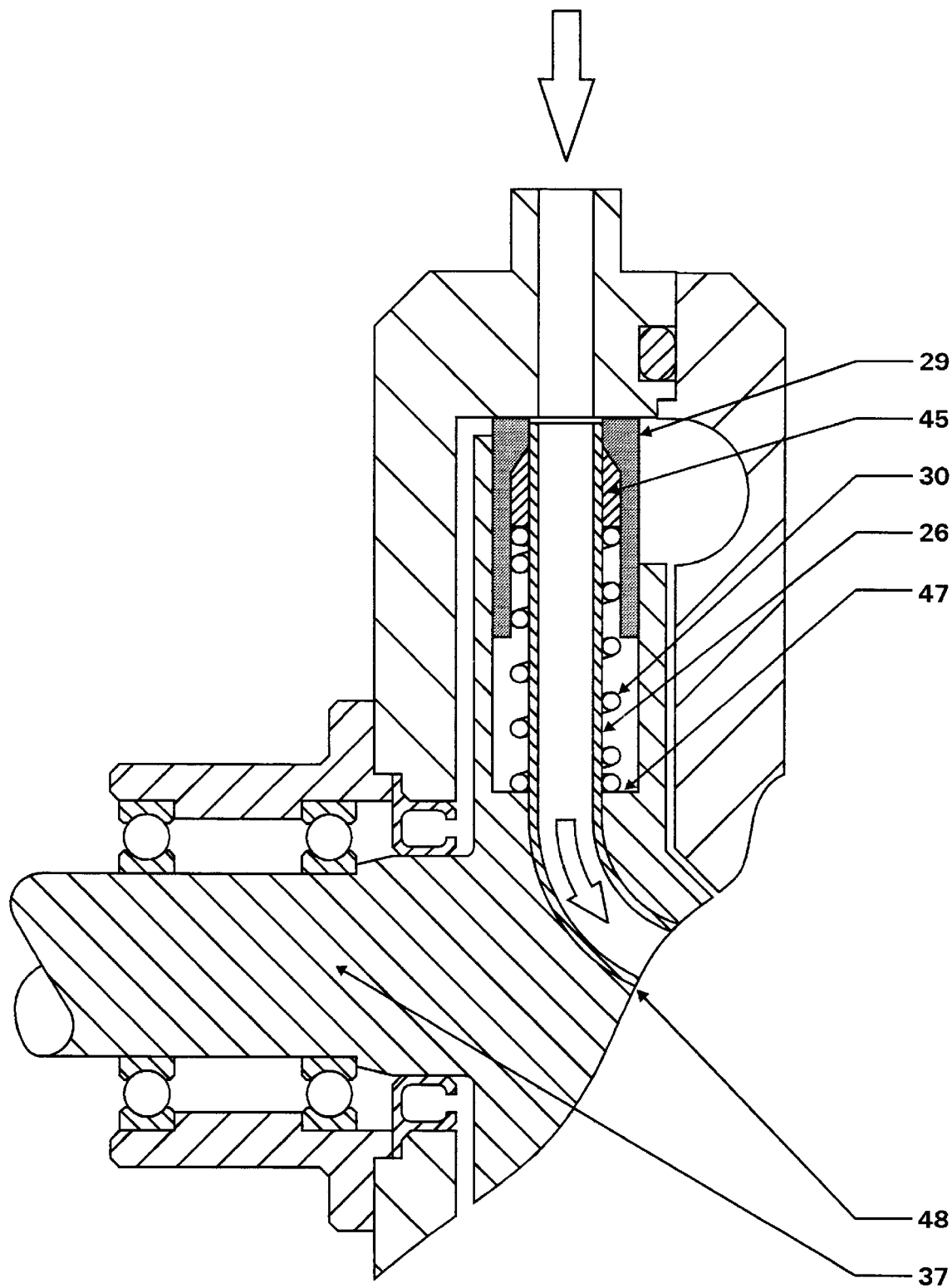
Fig. 11 Part sectional view - Selector valve

SELECTOR VALVE

This invention relates to a selector valve which may be used to control flow between a plurality of inputs and a single output or between a single input and a plurality of outputs. Although the invention will be primarily described in relation to a sampling valve which can take fluid flowing from any of a plurality of inlets and direct it to a single outlet, it will be appreciated that the invention is equally applicable to a distributor valve arrangement acting in the opposite way and to comparable structures and devices.

Typical known selector valves are describe in GB 995016D, U.S. Pat. No. 4,191,213B, U.S. Pat. No. 5,046,522B, WO87/02428 and U.S. Pat. No. 4,198,9641B.

In the prior known valves, for example the valve described in WO87/02428, and also in the known valve shown in FIGS. 1, 2 and 3 a known selector valve 10 has a plurality of selectable ports 11 each terminating at a sealing surface 12 which forms a path for and is slidingly engaged by a selector head 13 whose port 14 is surrounded by a seal member 15 urged against a surface 12 as by a spring 16. Referring now to FIGS. 2 and 3 it will be seen that as the seal member 15 traverses the mouths of the ports 11 in use there is a degree of wear over that central band 17 which engages the edges of the mouths of the ports 11. After some use that central band 17 tends to become more worn than the remainder of the seal member 15 and this wear is shown (in an exaggerated manner) as a central groove 18 in FIG. 3. It will be appreciated that the groove 18 effectively provides a leak path in the direction of arrow 19.

It will be appreciated that comparable problems will arise in relation to similar selector valves, for example the selector valve described in specification GB995016B wherein the selector head moves over a flat surface rather than over a cylindrical surface. It is an object of the invention to provide an improved selector valve.

The invention provides a selector valve having a plurality of selectable ports terminating at mouths in a sealing surface which can be traversed by a selector head having a seal member which provides a seal between a selected port and a port of the selector head, the seal member having, considered in its direction of travel relative to the selectable ports a central band which traverses those ports and lateral portions which do not traverse the ports, the areas of said lateral portions being selected so that the wear which they undergo during their traversing of the sealing surface without contact with the selectable ports is generally equal to the rate of wear of the central band which traverses the ports.

The invention also provides a selector valve having a plurality of selectable ports terminating at mouths in a sealing surface which can be traversed by a selector head having a seal member which provides a seal between a selected port and a port of the selector head, the seal member having, considered in its direction of travel relative to the selectable ports a central band which traverses those ports and lateral portions which do not traverse the ports, wherein the area of the lateral portions of the seal member are smaller than the area of the central band so as to wear at about the same rate as the central band.

The invention further provides a selector valve having a plurality of selectable ports terminating at mouths in a sealing surface which can be traversed by a selector head having a seal member which provides a seal between a selected port and a port of the selector head, the seal member having, considered in its direction of travel relative to the selectable ports a central band which traverses those ports and lateral portions which do not traverse the ports, wherein the areas of the lateral portions of the sealing face of the seal member are reduced so as to wear at about the same rate as the central band.

As it will be appreciated, the seal member has in the past generally been selected to be circular to uniformly surround the selected ports on the selector surface. In carrying out the invention it is possible for the circular seal member to be reduced in width in a direction transverse to its path of travel by having flats formed on it. Alternatively an elliptical shape can be chosen having its longer axis in the direction of travel.

A further problem arises in relation to such selector valves in the provision of a seal between a stem of the selector head and a static part of the valve. The selector head is usually mounted on the end of a (for example) "L" shaped length of ducting, one limb of which effects simple pivoting about its axis and the other of which carries the sealing head at its end. The first limb, at its end, must be sealed relative to static structure such as pipe work which will direct the selected input to, for example, analytic equipment.

It will be appreciated that for analytic equipment a high integrity rotary seal must be provided between the static parts and the rotating limb of the selector head. It is a further object of the invention to improve such a selector valve by reducing the standards required for an effective seal at that position.

The invention further provides a selector valve including a selector head comprising ducting having a first part which rotates about its axis and a second part which carries a selector seal at its free end, the free end of the first part being sealed against non-rotating structure by an annular sealing ring, wherein a static tube extends into the first part of the ducting.

The provision of the static tube enables samples to be taken from flow within the ducting upstream of the sealing ring thus making any leak at the sealing ring of lower significance. The portion of the ducting surrounding the tube can lead to an exhaust vent via the sealing ring. The invention also provides a sampling arrangement including a selector valve as aforesaid and including a plurality of sample sources capable of causing a given flow rate in the selector head conduit and in combination with destination equipment having a flow requirement less than the flow rate in the selector head ducting, excess flow in the ducting being allowed to pass outside the selector tube passed through the annular seal between the end of the ducting and static parts and be vented to waste.

The destination equipment can be analytic equipment such as a gas chromatograph.

The invention will be described further, by way of example, with reference to the accompany drawings wherein:

FIG. 1 is a plan view of a known selector valve;

FIG. 2 is an end elevation of a seal member of a selector head of the valve of FIG. 1;

FIG. 3 is a perspective view of the seal member;

FIG. 4 is a cross-sectional view of the selector of FIG. 1 modified in accordance with the invention;

FIG. 5 is a view similar to FIG. 2 but showing the invention;

FIG. 5a is an enlarged view of FIG. 5;

FIG. 5b is a perspective view of FIG. 5;

FIG. 6 is a view similar to FIG. 5 but showing a variation;

FIG. 11 shows a modification to the arrangements shown in FIGS. 7 and 8.

Figure 7:
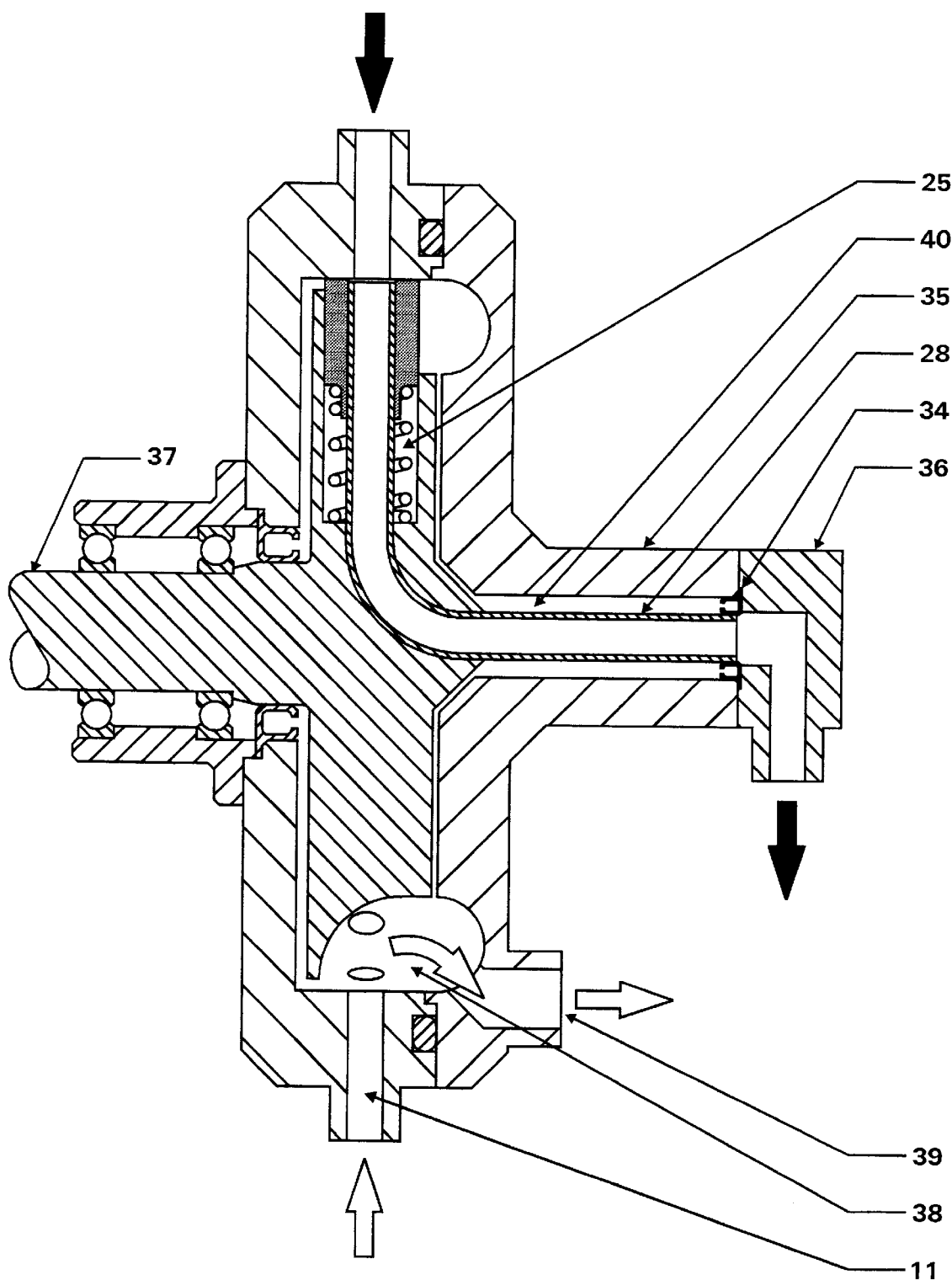
FIG. 7 is a cross-sectional view of a selector valve in accordance with the invention

Referring now to FIGS. 4 and 5 it will be seen that instead of the arrangement of FIGS. 1, 2 and 3 (which has already been described) a preferred valve of the invention has an annular body 21 providing a circular sealing surface 22 into which open the mouths 23 and a plurality of selectable inlet ports 24. A sealing head 25 includes one limb 26 of selector ducting 27 whose other limb 28 is disposed on and rotatable about an axis of the valve. The selector head 25 carries a seal member 29 which is urged by a spring 30 against surface 22 and has a sealing face which is shown in FIG. 5. As best seen in FIG. 5a the sealing face of the seal member 29 has a central band 31 which, in use, traverses the mouths 23. Lateral areas above and below the band 31 are indicated at 32 and 33.

As best seen in FIG. 5a the lateral areas 32 and 33 are reduced in size compared to the area of the band 31. The reduction in size is such that the area of the band 31 (ignoring the central aperture communicating with the ducting 26) is greater than the areas 32 and 33. This reduction in the size of the areas 32 and 33 means that the contact pressure imposes greater wear on the areas 32 and 33 during the sliding movement with the surface 22.

Thus, in use the central band 31 and the areas 32 and 33 wear in unison and the groove illustrated at 18 in FIG. 3 does not develop. Or, if it does, only develops after a prolonged period of use at which stage the seal can be replaced.

The valve 20 of FIG. 4 is more completely described in FIG. 7 and it will be seen that the sealing head 25 forms part of a distributor whose porting has a limb 28 sealed by annular seal 34 to part of a housing 35 to which is connected pipe work 36 which can lead to destination equipment, for example analytic equipment such as a gas chromatograph. The selector head is rotated by means of a shaft 37 and non-selected ports 11 vent to the interior 38 and exit via exhaust port 39. It will be appreciated that the interior of the housing 35 illustrated at 40 will be filled with un-selected fluid streams and therefor the integrity between the ducting 28 and that interior must be maintained quite highly by the seal 34. Any leakage through the seal 34 could cause entry of fluid into the sample.

Figure 8:
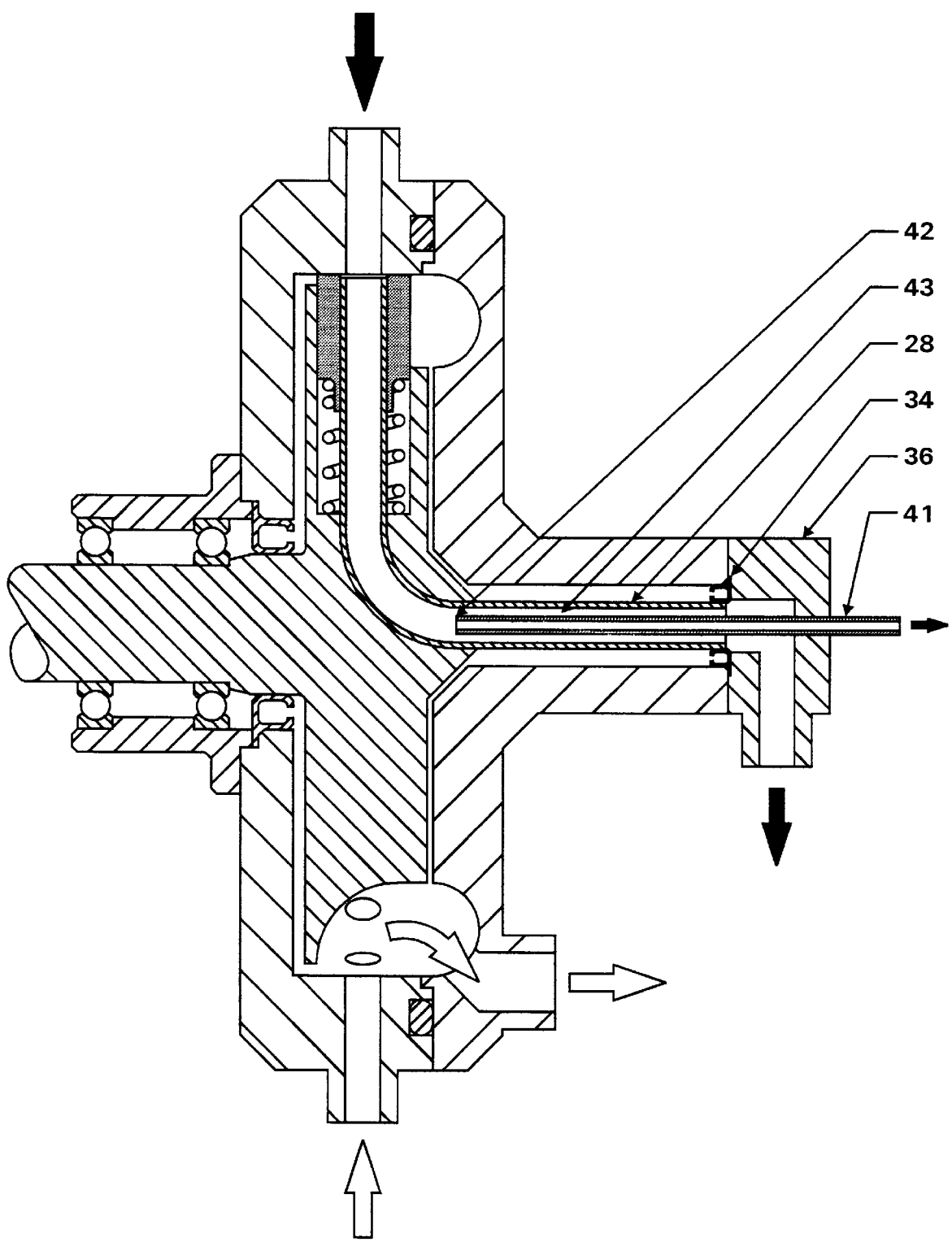
FIG. 8 is a view similar to FIG. 7 but showing the selector valve of FIG. 7 modified in accordance with a second feature of the present invention.

FIG. 8 illustrates how, in accordance with a second feature of the invention the danger of leakage at the seal 34 can be significantly reduced. Here, a sampling tube 41 passes fixedly through the pipe work 36 and enters telescopically into the ducting 28. The tube 41 lies on the axis of rotation of the selector head and therefore is a static item. The free end 42 is well upstream (considered in the direction of flow of sampled product) and therefore the product to be sampled enters via the open ended tube 42 passes down tube 41 and passes to its use destination. Excess flow carries on in the annular space 43 to exhaust. It will be appreciated that any leakage at the seal 34 does not affect the sample selected because it will be virtually impossible for any contaminant to pass, to the left in FIG. 8, from the seal 34 towards the inlet 42 against the flow in the space 43. This allows the seal 34 to be an item of less expensive and less critical construction and its inspection and maintenance, although necessary, can be reduced in frequency and therefore in cost.

Figure 10:
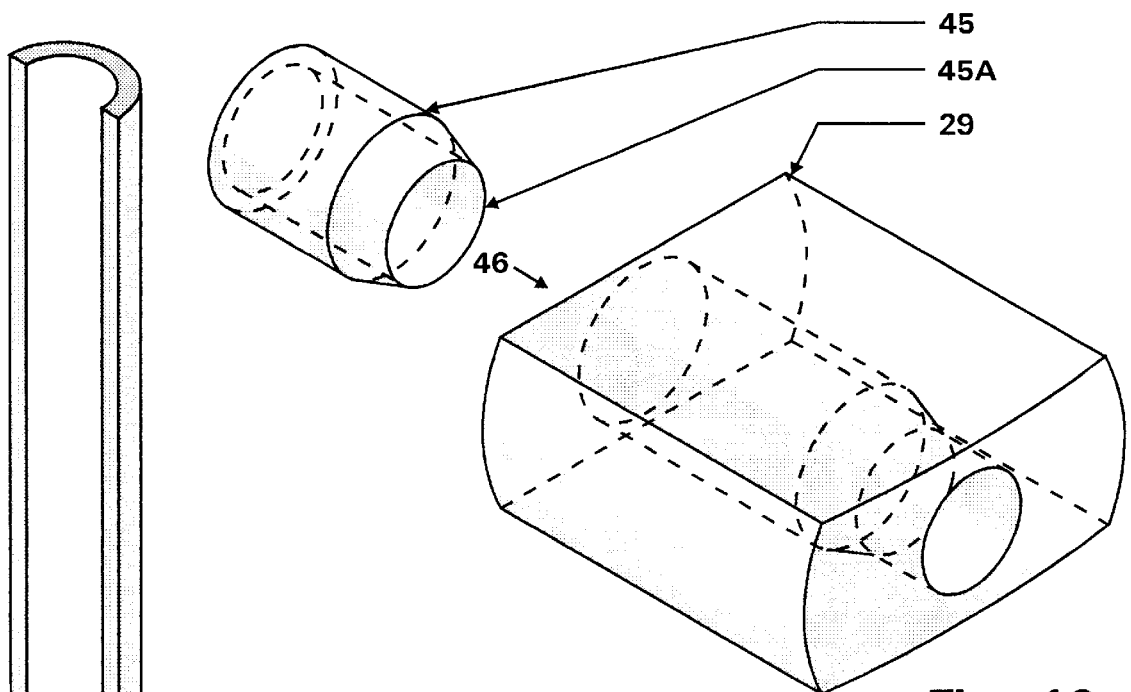
FIG. 10 shows to an enlarged scale a detail of the modification shown in FIG. 9.
Figure 9:
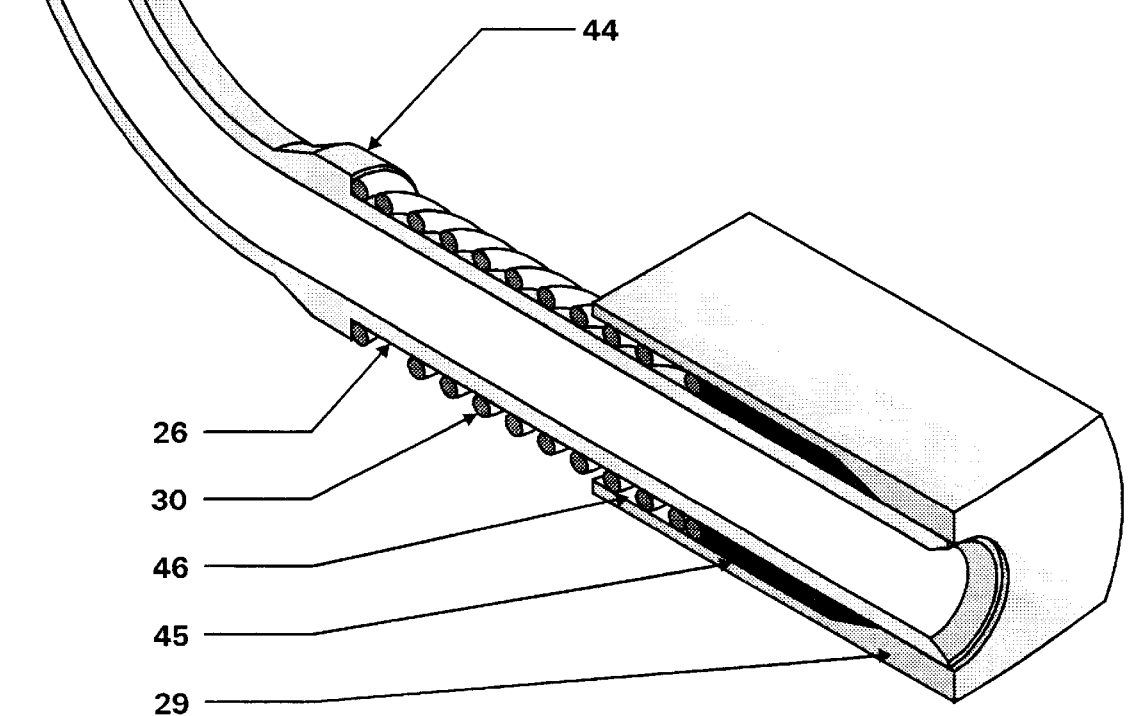
FIG. 9 shows a modification to the selector valves shown in FIGS. 5, 6 and 7.

Referring to FIGS. 9 and 10 there is shown a modification which can be applied to the selector valves shown in FIGS. 4, 5, 6, 7 and 8. Components similar to those in the previous figures have been accorded identical reference numbers. The spring (30) seats at one end against a shoulder (44) provided on the limb (26). The opposite end of the spring (30) seats against an inner sealing ferrule (45) which is mounted on the limb (26) and positioned within a recess (46) within the seal member (29).

The function of the sealing ferrule (45) is to prevent leakage along the path formed between the external diameter of the limb (26) and the internal diameter of the sealing member (29). This leakage increases with temperature due to the differential thermal expansion rates of the seal member which is formed from PTFE and the stainless steel limb (26).

The load exerted by the spring (30) acts on the sealing member (29) via the sealing ferrule (45). This spring loading forces the lip (45A) of the ferrule into intimate contact with the sealing member (29) and the limb (26) so forming a sliding seal.

The sealing takes place at a point very close to the open mouth of the port face and thus minimises accumulation of sample material trapped in the path mentioned above.

Referring to FIG. 11, the sealing ferrule (45) is shown being urged into contact with the sealing member (29) by the spring (30) which bears at one end against a seating (47) provided on the shaft (37) and the limb (26) extends through a duct (48) formed in the shaft (37).

The invention is not limited to the precise details of the foregoing and variations can be made thereto. Clearly the invention (except for the optional feature of the static sampling tube 41) is applicable to valves wherein there is either distribution or sampling and wherein the selector head moves over a flat, conical or other surface into which extend a number of mouths of selectable ports.

Many other variations are possible within the scope of the invention.

I claim:

1. A selector valve comprising a plurality of selectable ports terminating at mouths in a sealing surface; a selector head that traverses the sealing surface, the selector head having a seal member which provides a seal between a selected port and a port of the selector head, the seal member being in constant contact with the sealing surface and having, considered in its direction of travel relative to the selectable ports, a central band which traverses the selectable ports and lateral portions which do not traverse the selectable ports, a width of the central band being equal to a width of the selected port and a length of the central band being greater than a length of the lateral portions, and the area of the lateral portions being selected so that the wear which the lateral portions undergo during their traversing of the sealing surface without contact with the selectable ports is generally equal to the rate of wear of the central band which traverses the selectable ports.

2. A selector valve as claimed in claim 1, wherein the areas of the lateral portions of the seal member are smaller than the area of the central band so as to wear at about the same rate as the central band.

3. A selector valve as claimed in claim 1, wherein the seal member has a truncated circular surface providing the seal between the selected port and the port of the selector head, the truncated circular surface being defined by a circular area reduced in width in a direction transverse to its path of travel by having flats along cords of the circular area, the cords being parallel to the path of travel.

4. A selector valve as claimed in claim 1, wherein the seal number has a surface providing the seal between the selected port and the port of the selector head, the surface being of generally elliptical cross section having its longer axis in the direction of travel.

5. A selector valve as claimed in claim 1, wherein the selector head further comprises ducting having a first part which rotates about its axis and a second part which carries the seal member at its free end, a free end of the first part being sealed against a non-rotating structure by an annular sealing ring, wherein a static tube extends into the first part of the ducting.

6. A selector valve as claimed in claim 5, wherein a portion of the ducting surrounding the static tube leads to an exhaust vent via the sealing ring.

7. A selector valve as claimed in claim 6, further comprising a plurality of sample sources capable of causing a given flow rate in the selector head ducting in combination with destination equipment having a flow requirement less than the flow rate in the selector head ducting, excess flow in the ducting being allowed to pass outside the static tube, through the annular seal, between the end of the ducting and the non-rotating structure and vented to waste.

8. A selector valve as claimed in claim 7, wherein the destination equipment is analytic equipment.

9. A selector valve as claimed in claim 8, wherein the analytic equipment is a gas chromatograph.

10. A selector valve, comprising, a plurality of selectable ports terminating at mouths in a sealing surface;

a selector head that traverses the sealing surface, the selector head having a seal member which provides a seal between a selected port and a port of the selector head, the seal member being in constant contact with the sealing surface and having, considered in its direction of travel relative to the selectable ports, a central band which traverses the selectable ports and lateral portions which do not traverse the selectable ports, a width of the central band being equal to a width of the selected port and a length of the central band being greater than a length of the lateral portions, and the area of the lateral portions being selected so that the wear which the lateral portions undergo during their traversing of the sealing surface without contact with the selectable ports is generally equal to the rate of wear of the central band which traverses the selectable ports; and a force applying member that applies a force to the seal member such that the seal member is maintained in constant contact with the sealing surface.

11. A selector valve as claimed in claim 10, wherein the areas of the lateral portions of the seal member are smaller than the area of the central band so as to wear at about the same rate as the central band.

12. A selector valve as claimed in claim 10, wherein the seal member has a truncated circular surface providing the seal between the selected port and the port of the selector head, the truncated circular surface being defined by a circular area reduced in width in a direction transverse to its path of travel by having flats along cords of the circular area, the cords being parallel to the path of travel.

13. A selector valve as claimed in claim 10, wherein the seal member has a surface providing the seal between the selected port and the port of the selector head, the surface being of generally elliptical cross section having its longer axis in the direction of travel.

14. A selector valve as claimed in claim 10, wherein the selector head further comprises ducting having a first part which rotates about its axis and a second part which carries the seal member at its free end, a free end of the first part being sealed against a non-rotating structure by an annular sealing ring, wherein a static tube extends into the first part of the ducting.

15. A selector valve as claimed in claim 14, wherein a portion of the ducting surrounding the static tube leads to an exhaust vent via the sealing ring.

16. A selector valve as claimed in claim 15, further comprising a plurality of sample sources capable of causing a given flow rate in the selector head ducting in combination with destination equipment having a flow requirement less than the flow rate in the selector head ducting, excess flow in the ducting being allowed to pass outside the static tube, through the annular seal, between the end of the ducting and the non-rotating structure and vented to waste.

17. A selector valve as claimed in claim 16, wherein the destination equipment is analytic equipment.

18. A selector valve as claimed in claim 17, wherein the analytic equipment is a gas chromatograph.

19. A selector valve as claimed in claim 10, wherein the force applying member is a spring.

* * * * *